US00PP20685P2

(12) United States Plant Patent
Jandrew

(10) Patent No.: US PP20,685 P2
(45) Date of Patent: Jan. 26, 2010

(54) ***PENSTEMON* PLANT NAMED 'PENI LAVER'**
(50) Latin Name: *Penstemon hartwegii*
Varietal Denomination: Peni Laver

(75) Inventor: Jason Jandrew, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/316,294

(22) Filed: Dec. 11, 2008

(51) Int. Cl.
*A01H 5/00* (2006.01)

(52) U.S. Cl. ..... Plt./465
(58) Field of Classification Search ..... Plt./465
See application file for complete search history.

*Primary Examiner*—Kent L Bell
(74) *Attorney, Agent, or Firm*—S. Matthew Edwards

(57) ABSTRACT

A new *Penstemon* plant named 'Peni Laver' particularly distinguished by the large purple-lavender flower color, upright and medium-compact plants, strong stems, early flowering and good floriferiousness.

1 Drawing Sheet

Latin name of the genus and species of the plant claimed: *Penstemon hartwegii.*

Varietal denomination: 'Peni Laver'.

BACKGROUND OF THE NEW PLANT

The present invention comprises a new *Penstemon*, botanically known as *Penstemon hartwegii,* and hereinafter referred to by the variety name 'Peni Laver'.

'Peni Laver' is a product of a planned breeding program. The new cultivar 'Peni Laver' has large purple-lavender flower color, upright and medium-compact plants, strong stems, early flowering and good floriferiousness.

'Peni Laver' originated from a hybridization in a controlled breeding program in Gilroy, Calif. USA. The female parent was an unpatented hybrid seedling identified as '101-2' with white color. '101-2' has longer internodes and is later to flower than 'Peni Laver.'

The male parent of 'Peni Laver' was an unpatented hybrid seedling identified as '104-1' with appleblossom color. '104-1' has a taller, less branched plant and is later to flower than 'Peni Laver'.

'Peni Laver' was selected as one flowering plant within the progeny of the stated cross in April 2006 in a controlled environment in Gilroy, Calif. USA. The pollination took place in July 2005 and the seed sown in October 2005 all in Gilroy Calif. USA.

The first act of asexual reproduction of 'Peni Laver' was accomplished when vegetative cuttings were taken from the initial selection in the April 2006 in a controlled environment in Gilroy, Calif. USA.

Horticultural examination of plants grown from cuttings of the plant initiated in April 2006 in Gilroy, Calif. USA, and continuing thereafter, has demonstrated that the combination of characteristics as herein disclosed for 'Peni Laver' are firmly fixed and are retained through successive generations of asexual reproduction.

'Peni Laver' has not been observed under all possible environmental conditions. The phenotype may vary significantly with variations in environment such as temperature, light intensity and day length.

A Plant Breeder's Right for this cultivar was applied for in Canada on Dec. 24, 2007. 'Peni Laver' has not been made publicly available more than one year prior to the filing of this application.

DESCRIPTION OF DRAWING

The accompanying photographic drawing shows typical flower and foliage characteristics of 'Peni Laver' with colors being as true as possible with an illustration of this type.

The photographic drawing shows 2 flowering potted plants of the new variety in a gallon pot and a close-up of the flowers.

The plants were grown and photographed in Gilroy, Calif. USA in July 2008.

DETAILED BOTANICAL DESCRIPTION

The measurements were taken in Gilroy, Calif. USA, in March 2008 on plants that were growing in gallon pots in a greenhouse trial. These plants were about 3 months old.

Color chart used: Royal Horticultural Society Colour Chart (R.H.S.) 2001

BRIEF SUMMARY OF INVENTION

The following observations, measurements, and comparisons describe plants grown in Gilroy, Calif. USA. The following traits have been repeatedly observed and are determined to be basic characteristics of the new variety. The combination of these characteristics distinguishes this *Penstemon* as a new and distinct variety.

TABLE 1

DIFFERENCES BETWEEN THE NEW VARIETY 'PENI LAVER' AND A SIMILAR VARIETY

| | 'Peni Layer' | 'Pheni Vio' (U.S. Plant Pat. No. 17,933) |
|---|---|---|
| Flower color | RHS 77A | RHS N77A |
| Leaf size/margin | Smaller/serrulate | Larger/weakly crenate |
| Plant habit | More compact | Less compact |
| Flowering response | Earlier | Later |

Plant:
*Plant habit.*—Upright, semi-compact, strong stems.
*Plant height.*—23–28 cm.
*Plant width.*—30–35 cm.
Foliage:
*Arrangement.*—Opposite and decussant.
*Immature, leaf color, upper surface.*—Darker than RHS 144A.
*Lower surface.*—RHS 138B.
*Mature, leaf color, upper surface.*—RHS 137A.
*Lower surface.*—RHS 138B.
*Length.*—8.5–9.2 cm.
*Width.*—2.4–2.8 cm.
*Shape.*—Lanceolate.
*Base shape.*—Attenuate.
*Apex shape.*—Acute.
*Margin.*—Serrulate.
*Texture.*—Pubescence on both sides.
*Color of veins, upper surface.*—RHS 144B.
*Color of veins, lower surface.*—RHS 144B.
Stem:
*Quantity of main branches per plant.*—3–5.
*Quantity of leaves per lateral branch.*—6–10.
*Color of stem.*—RHS 44A to 44B.
*Length of stem.*—20–25 cm.
*Diameter.*—0.3–0.4 cm.
*Length of internodes.*—1.0–3.0 cm.
*Texture.*—Sparse short pubescence.
Inflorescence:
*Type.*—On first flowering it appears to be a raceme, then matures to more of a thyrse with short peduncles emerging at the nodes in opposite arrangement, each peduncle bearing 5–7 flowers or buds at various stages of development; the flowers are held somewhat horizontally.
*Blooming habit.*—Intermittent; removing of spent flowers enhances development of new flowers.
*Number of inflorescences per plant.*—10–14; early terminal pinching of apices enhances formation of more racemes.
*Raceme color.*—RHS 144B.
*Raceme length.*—14–20 cm.
*Raceme texture.*—Short pubescence.
*Color of peduncle.*—RHS 144B.
*Length of peduncle.*—0.7–1.0 cm.
*Diameter of peduncle.*—0.1 cm.
*Texture.*—Short pubescence; glandular hairs.
*Color of pedicel.*—RHS 144B.
*Length of pedicel.*—0.6–0.8 cm.
*Diameter of pedicel.*—0.1 cm.
*Texture.*—Short pubescence; glandular hairs.
Corolla:
*Form.*—Zygomorphic and single; funnel-shaped with the petals mainly fused at base; 5 free lobed, opening outward.
*Fragrance.*—None.
*Lastingness of individual florets.*—About 5–7 days.
*Width of floret.*—3.2–3.5 cm.
*Depth of floret.*—3.4–3.7 cm.
*Color of upper lobes, upper surface.*—RHS 72A with RHS 71A margins maturing to lighter than RHS 77A to 77B with RHS 72A margins.
*Color of upper lobes, lower surface.*—RHS N155B with RHS 70A margins.
*Length of upper lobes.*—1.0–1.2 cm.
*Width of upper lobes.*—1.2–1.3 cm.
*Color of lateral lobes, upper surface.*—Same as upper lobes.
*Color of lateral lobes, lower surface.*—Same as upper lobes.
*Length of lateral lobes.*—1.1–1.3 cm.
*Width of lateral lobes.*—1.3–1.5 cm.
*Color of lower mid-lobe, upper surface.*—Same as upper lobes.
*Color of lower mid-lobe, lower surface.*—Same as upper lobes.
*Length of lower mid-lobe.*—1.2–1.4 cm.
*Width of lower mid-lobe.*—1.2–1.4 cm.
*Apex shape.*—Rounded to slightly obtuse.
*Margin.*—Entire.
*Petal texture.*—Papillose and some slight pubescence on both surfaces.
*Corolla color, inside.*—RHS N155B but whiter.
*Corolla color, outside.*—RHS N155B but whiter; sometimes blushed with RHS 77B to 77C on the upper side.
*Corolla length.*—2.9–3.1 cm.
Bud (just before opening):
*Color.*—Darker than RHS 71 A with RHS N79B at the apex.
*Length.*—1.7–2.2 cm.
*Width.*—1.0–1.2 cm.
*Shape.*—Oblong.
*Number of sepals.*—5, fused at base.
*Color of sepals.*—RHS 144B.
*Length of sepals.*—0.7–0.8 cm.
*Width of sepals.*—0.3–0.6 cm.
*Sepal shape.*—Ovate.
*Apex shape.*—Acute.
*Margins.*—Entire.
*Texture.*—Pubescent; glandular hairs.
Reproductive organs:
*Pistil.*—1.
*Style color.*—RHS N155B.
*Style length.*—2.9–3.0 cm.
*Stigma color.*—RHS N155B.
*Number of anthers.*—5, 4 of which are fertile.
*Color of filaments.*—RHS N155B.
*Length filaments.*—2.9–3.0 cm.
*Color of pollen.*—RHS 155C.
*Pollen amount.*—Abundant.
*Fertility/seed set.*—Not observed on this hybrid.
Disease/pest resistance: Disease resistance or susceptibility has not been observed on this hybrid

What is claimed is:

1. A new and distinct variety of *Penstemon* plant named 'Peni Laver', substantially as illustrated and described herein.

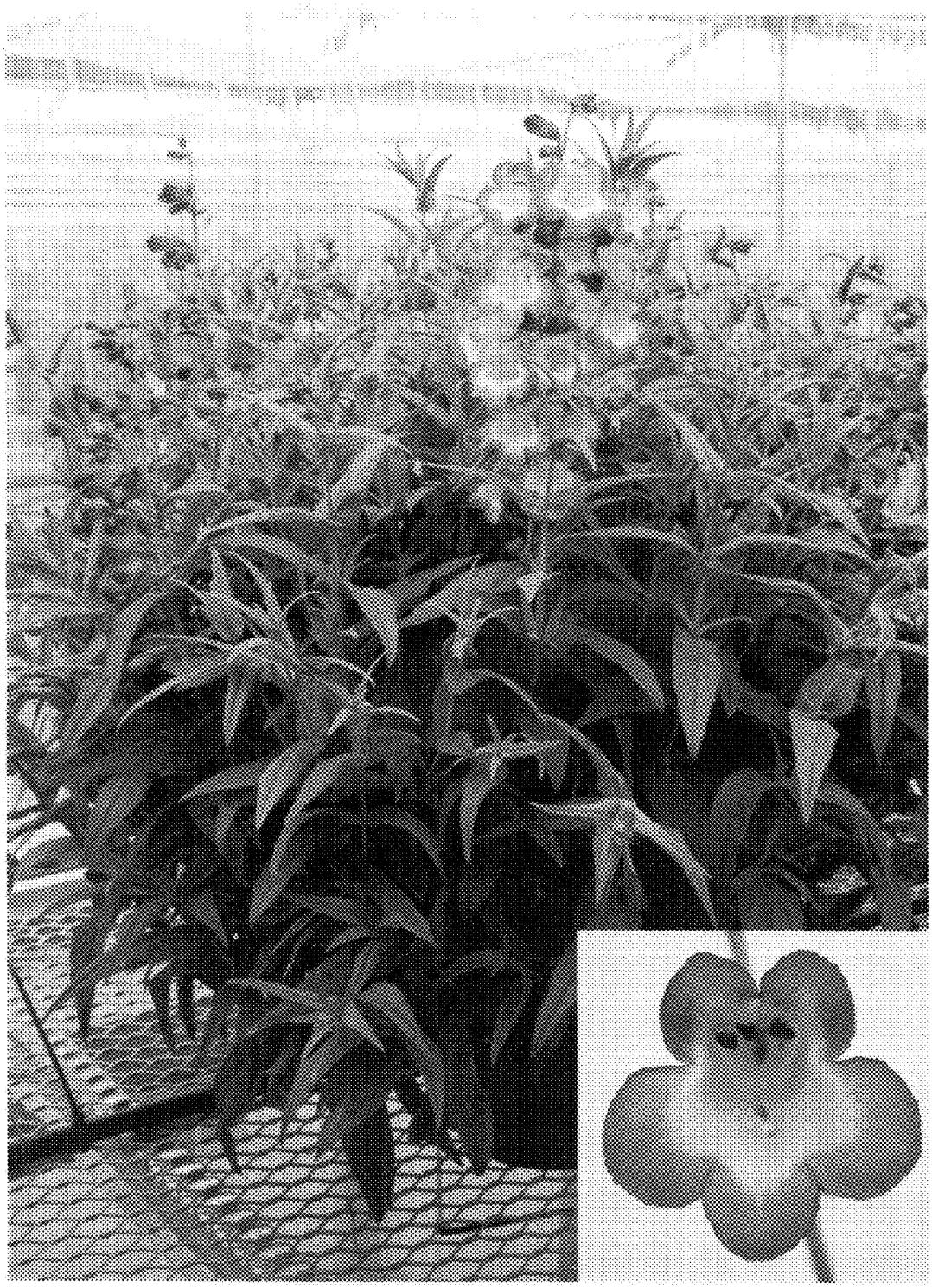

* * * * *